| United States Patent [19] | [11] | 4,431,416 |
|---|---|---|
| Niznick | [45] | Feb. 14, 1984 |

[54] ENDOSSEOUS DENTAL IMPLANT SYSTEM FOR OVERDENTURE RETENTION, CROWN AND BRIDGE SUPPORT

[75] Inventor: Gerald A. Niznick, Encino, Calif.

[73] Assignee: A & L Investment Company, Encino, Calif.

[21] Appl. No.: 372,945

[22] Filed: Apr. 29, 1982

[51] Int. Cl.³ ............................................... A61C 8/00
[52] U.S. Cl. ..................................................... 433/174
[58] Field of Search ................ 433/173, 174, 175, 176

[56] References Cited

U.S. PATENT DOCUMENTS

| 3,499,222 | 3/1970 | Linkow et al. | 433/174 |
| 4,180,910 | 1/1980 | Straumann | 433/173 |

*Primary Examiner*—Robert Peshock
*Attorney, Agent, or Firm*—Fred Flam

[57] ABSTRACT

One part of the implant comprises a rigid screw anchor of substantially uniform diameter. The anchor has intermediate peripheral threads to engage the bone tissue at a prepared recess. The lower end of the anchor is hollow, peripherally perforated and open at the end to surround a bone core projecting from the bottom of the prepared recess. The upper end of the anchor has a relatively deep wrench socket for rotation of the anchor and for reception of a companion pillar part. The pillar part is made of slightly flexible plastic material that can approximate a prepared tooth to serve as a single tooth replacement or as a support for a fixed bridge. Optionally, the pillar can provide a platform that forms or mounts one of two companion elements of a connector structure such as for overdenture retention. The anchor can be altered in length not only at the bottom, but also at the top, without changing the manner in which the anchor cooperates with the later placed pillar.

24 Claims, 20 Drawing Figures

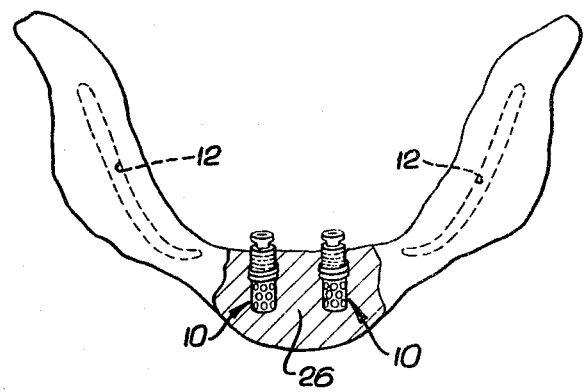
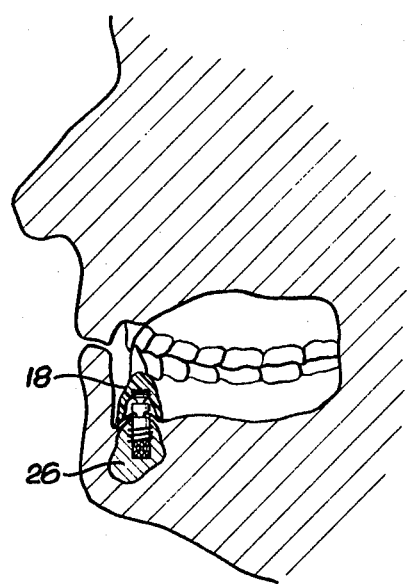
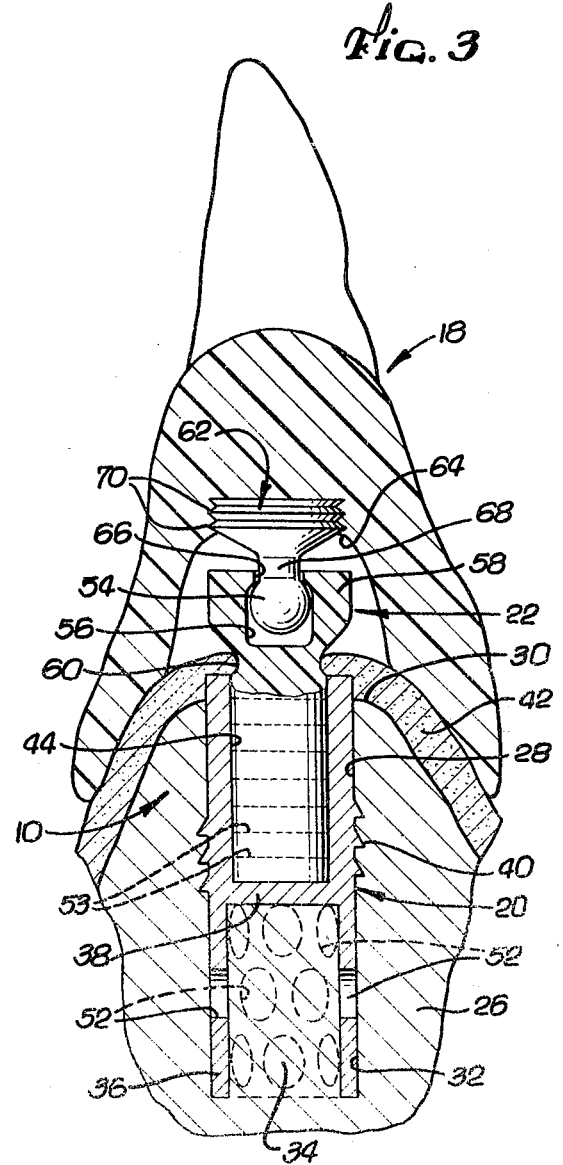
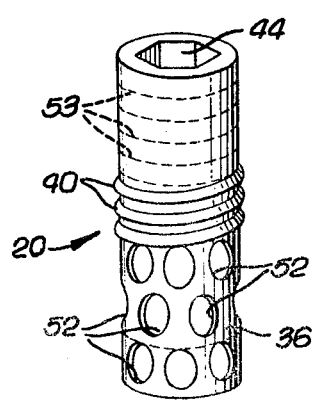

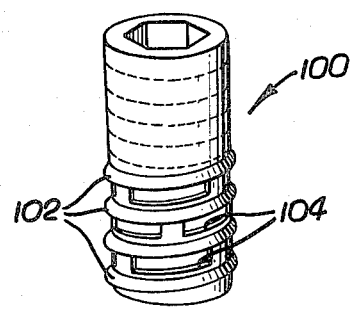
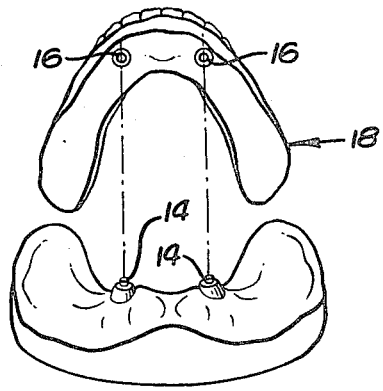
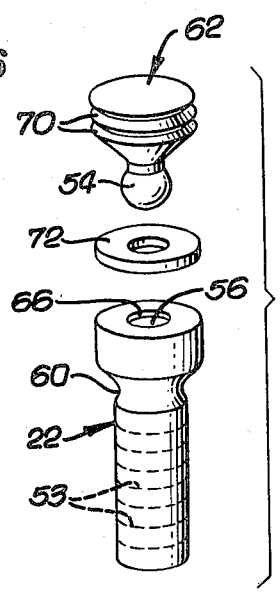
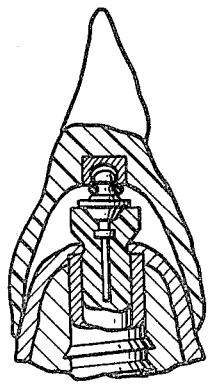
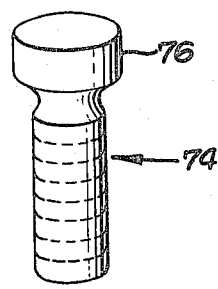
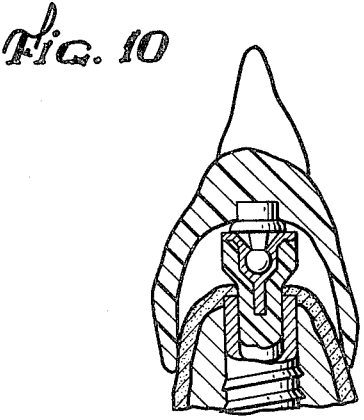

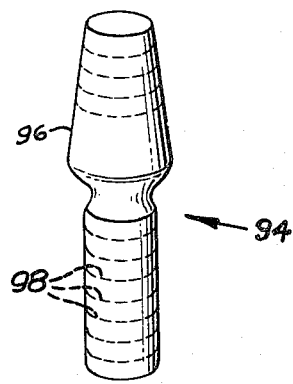
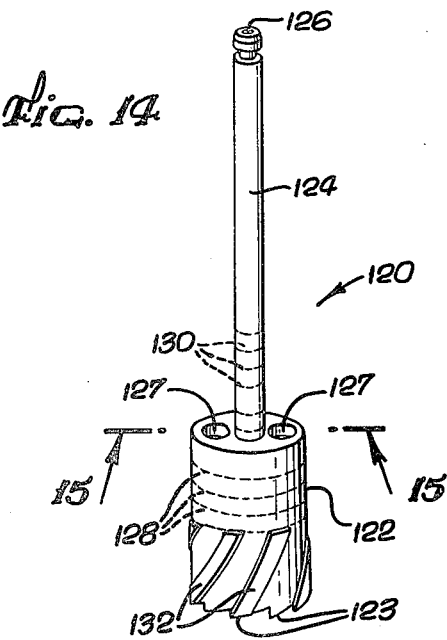
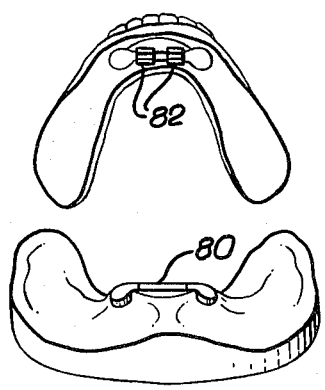
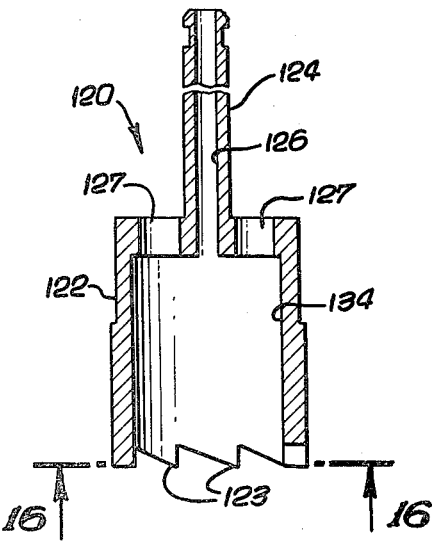
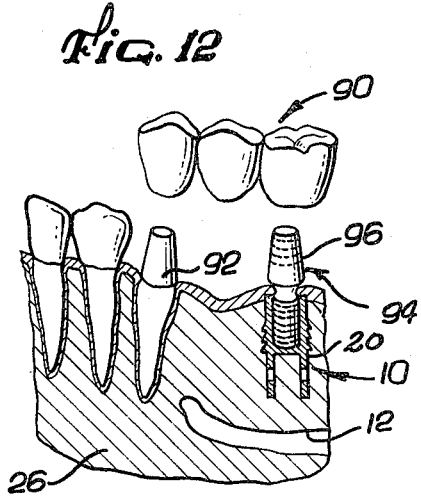
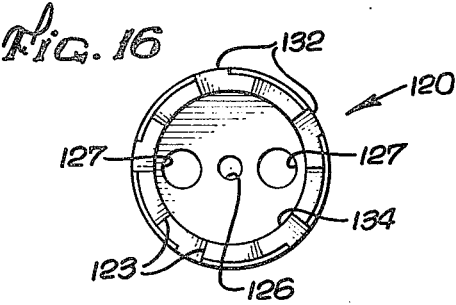

Fig. 17
A 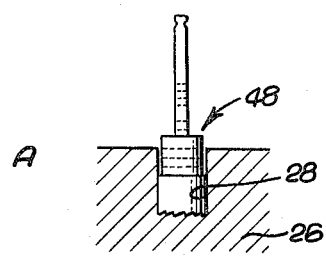
B 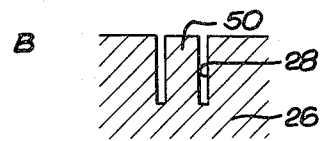
C 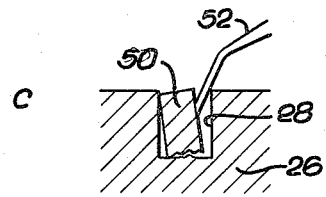
D 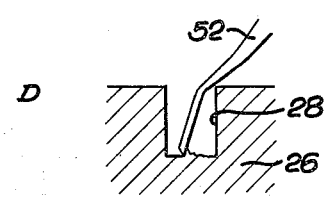
E 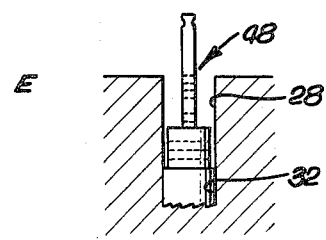
F 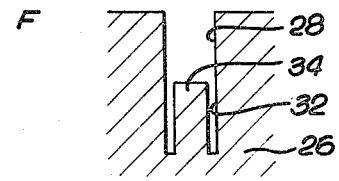
G 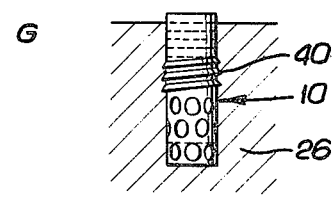
Fig. 18
A 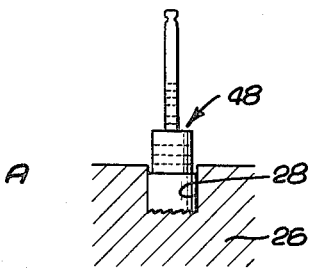
B 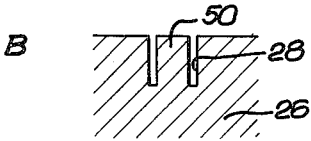
C 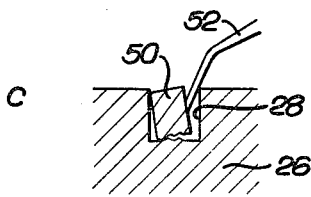
D 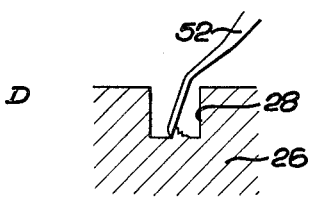
E 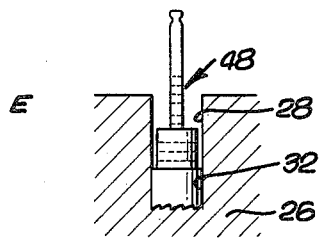
F 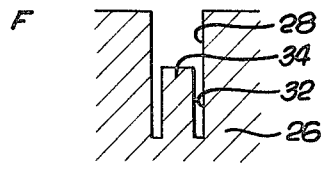
G 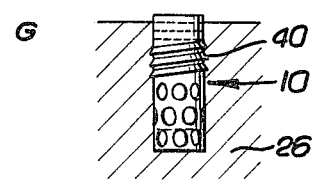
Fig. 19
A 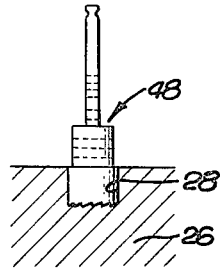
B 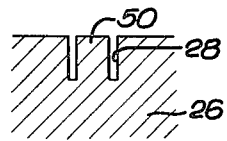
C 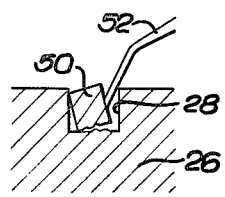
D 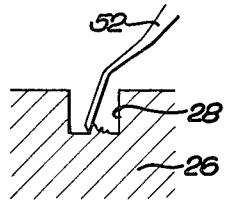
E 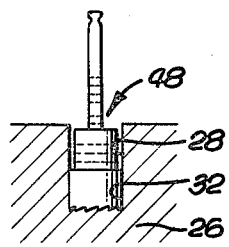
F 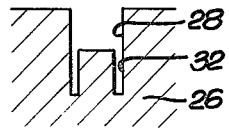
G 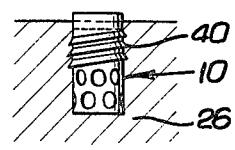

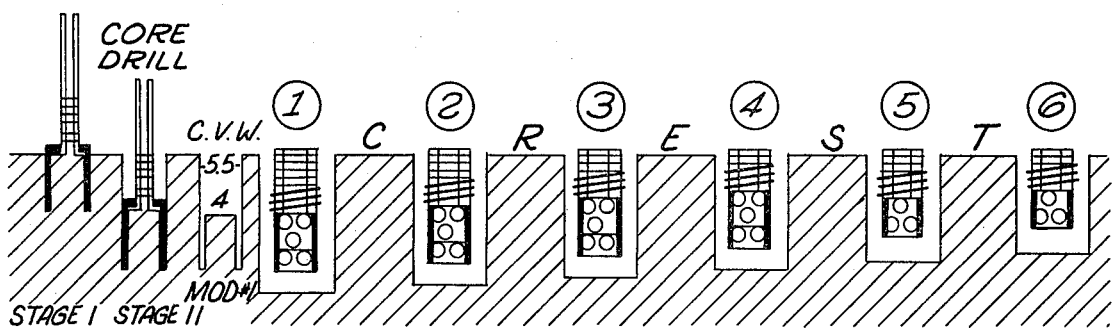

Fig. 20

SELECT, PLACE AND MODIFY FOR MAXIMUM USE OF AVAILABLE BONE
— PLACE NECK 1mm ABOVE CREST OF BONE
— PLACE THREADS AT LEAST 1mm BELOW CREST OF BONE
— ELIMINATE EXPOSED PORTION OF THREADS

TWO DIAMETERS — CORE-VENT N : 4.5mm CORE  5.0mm OSD OF THREADS
              — CORE-VENT W : 5.5mm CORE  6.3mm OSD OF THREADS
SIX LENGTHS — MAXIMUM = 16mm (5mm NECK + 3½mm THREADS + 7.5mm CORE)

| MODIFI-CATION # | AVAILABLE BONE | SHORTEN NECK | REMOVE ONE ROW OF VENTS | PREPARE IMPLANT SITE WITH 7½mm CORE DRILL | |
|---|---|---|---|---|---|
| | | | | STAGE I CORE LINES | STAGE II SHANK LINES |
| 1 | 15mm+ | 0 | 0 | FULL DEPTH TOP LINE | FULL DEPTH TOP LINE |
| 2 | 14mm | -1mm | 0 | 2nd LINE | 2nd LINE |
| 3 | 13mm | -2mm | 0 | 3rd LINE | 3rd LINE |
| 4 | 12mm | -3mm | 0 | BOTTOM LINE | 4th LINE |
| 5 | 11mm | -2mm | -2½mm | 3rd LINE | 5th LINE |
| 6 | 10mm | -3mm | -2½mm | BOTTOM LINE | BOTTOM LINE |

ENDOSSEOUS DENTAL IMPLANT SYSTEM FOR OVERDENTURE RETENTION, CROWN AND BRIDGE SUPPORT

FIELD OF THE INVENTION

This invention relates to dental implants and, particularly, to endosseous implants.

BACKGROUND OF THE INVENTION

Successful endosseous implants date from about 1968, at which time a biocompatible metal blade was fitted into a prepared elongated receptor site. The blade itself was perforated or vented to allow bone and blood vessels to reunite readily. A projecting metal head, either unitary with or detachable from the blade, provided an anchor for attachment of a fixed bridge. Another endosseous metal implant design is the basket type having a projecting metal head. This implant is used specifically for partial support of a fixed bridge. Neither the blade nor the basket implant is designed or adapted for use as an anchor for overdentures or for use as a freestanding single tooth replacement to support a single crown. Solid root-shaped ceramic implants such as sold by Miter Co. of Worthington, Ohio, are used for support of a single tooth replacement and for partial support of a fixed bridge, but are not adapted for use as an anchor for overdentures. Ceramic implants are stiff, brittle and bulky. They are not susceptible to specific case modifications.

The screw-type implants have been attempted for overdenture retention. The screw-type implant, such as sold by Zest Anchors, Inc. of San Diego, Calif., and Institut Shausman AG of Waldenburg, Switzerland, utilizes a solid self-tapping screw.

A relatively small percentage of such sold screw-type implants have long term success. Commonly, failure occurs due to inadequate reattachment of bone tissue to the screw. Even in cases that appear to provide good connection, bone deterioration at the neck of the implant, as well as bone resorption at the threads, is often radiographically detected.

The basket type implant utilizes an inverted cylindrical cage or "basket" that fits about a cylindrical bone core and into an annular recess that is formed by an incomplete cut of a trephine drill. Perforations or vents in the basket or cage allow bone and blood vessels to reunite. A good mechanical fixation is accomplished, but only after a fairly lengthy healing period. Clearly, the screw-type implant is advantageous from the standpoint of immediate structural connection.

The primary object of the present invention is to provide an implant system (1) that has a higher success rate as compared to the blade, screw and basket types of metal implants and compared to ceramic implants; (2) that is versatile enough to be used for the retention of an overdenture, the support of a fixed bridge, or the support of a crown for a single tooth replacement; (3) that isolates the endosseous portion from the oral cavity during the healing state; and (4) that allows the actual head portion to become a part of the working laboratory model during construction of the fixed prosthesis capable of modification without annoyance to the patient prior to completion of the final prosthesis.

Another important object of this invention is to provide an implant system that utilizes a screw anchor so constructed that it can be precisely trimmed (1) to fit the specific jawbone recess; (2) to locate the screw threads at the required minimum distance beneath the bone crest; and (3) to locate the top of the anchor just slightly above the bone crest.

Another object of this invention is to provide a two-part endosseous implant that includes as one part, a semi-rigid (or semi-flexible) pillar supported by the screw anchor adjacent the level of the bone crest to maximize stability relative to lateral forces.

Another object of this invention is to provide a plastic pillar of this character that has a flexural modulus of elasticity close to that of bone tissue itself and that can be trimmed, as need be, to change flexural characteristics closely to approximate the slight mobility found in natural teeth. Occlusal stresses are thus evenly transmitted to the bone. Moreover, by providing a slight yielding or shock absorbing function, harmful stresses upon application of lateral occlusal forces are reduced. Avoidance of localized stress promotes an intimate and lasting contact between the bone and the metal screw anchor, not achieved by other implant systems.

Still another object of this invention is to provide a special trephine drill to facilitate the precise preparation of the jawbone recess.

SUMMARY OF THE INVENTION

In order to achieve the foregoing objects, I provide a biocompatible implantable metal screw anchor that has an inverted perforated core at its lower end, a hollow wrench socket at its upper end, and self-tapping threads at the medial portion. The receptor site is prepared by drilling a cylindrical recess followed by drilling a deep annular kerf at the bottom of the recess, leaving a bone core. The available jawbone structure determines the size of the recess. The anchor is sized to the recess. Screw advancement seats the core of the anchor about the bone core. The top of the anchor is located 1 mm above the crest of the bone, ultimately to be surrounded by gum tissue. The screw threads are located at least 1 mm below the crest of the bone. A chart assists the sizing operations.

The attachment and preparation of the companion pillar may be delayed to allow healing. In that event, a plastic rod of a matching diameter to the socket is inserted for later removal and the gum tissue is sutured to close over the parts. Sooner or later the plastic pillar is installed in the socket. The plastic pillar can take a variety of forms, depending upon the requirements. It may simulate a tooth stump for a bridge; it may be prepared as a detachable connector for a denture; it may be crowned as a single tooth replacement. Flexural characteristics can be adjusted readily by slight physical alterations.

BRIEF DESCRIPTION OF THE DRAWINGS

A detailed description of the invention will be made with reference to the accompanying drawings wherein like numerals designate corresponding parts in the several figures. These drawings, unless described as diagrammatic or unless otherwise indicated, are to scale.

FIG. 1 is a diagrammatic study corresponding to a commonly used radiographic development of the patient's lower jaw, showing two screw anchors implanted at the cuspid region of the alveolar bone for overdenture retention.

FIG. 2 is a diagrammatic vertical sectional view of a patient's mouth and illustrating in section, one of a pair of implants used to anchor an overlay denture.

FIG. 3 is an enlarged axial sectional view of one of the implants in situ, part of the surrounding bone and gum tissue being shown in section.

FIG. 4 is a perspective view of the metal screw anchor part of the implant.

FIG. 5 is a diagrammatic view showing, by the aid of a plastic mouth model, the manner of connection of an overlay denture.

FIG. 6 is an exploded view illustrating the preferred attachment structure together with a spacer.

FIG. 7 is a perspective view of an unprepared plastic pillar that can support, or be formed to provide, one part of a two part connector.

FIG. 8 is a perspective view of a modified screw anchor.

FIGS. 9 and 10 are sectional views similar to FIG. 3, showing two different commercially available attachments utilizing the pillar of FIG. 7.

FIG. 11 discloses a third commercially available attachment anchored to the new implant.

FIG. 12 discloses the implant used to support one end of a bridge, the implant including a pillar with a tapered head approximately the shape of a prepared tooth.

FIG. 13 is a perspective view of the pillar of FIG. 12.

FIG. 14 is a pictorial view of a special trephine drill for use in preparing the receptor site.

FIG. 15 is an enlarged axial sectional view of the drill taken along a plane corresponding to line 15—15 of FIG. 14.

FIG. 16 is an end elevational view of the drill and taken in the direction of the plane 16—16 of FIG. 15.

FIG. 17 diagrammatically illustrates the successive steps in the preparation of the receptor site and the placement of the implant.

FIGS. 18 and 19 are diagrammatic views similar to FIG. 17, but illustrating the procedures applied with less available jawbone.

FIG. 20 is a drawing of a transparent chart used for determining proper configuration of the anchor.

DETAILED DESCRIPTION OF PREFERRED EMBODIMENT

The following detailed description is of the best presently contemplated modes of carrying out the invention. This description is not to be taken in a limiting sense, but is made merely for purposes of illustrating the general principles of the invention, since the scope of the invention is best defined by the appended claims.

Structural and operational characteristics attributed to forms of the invention first described shall also be attributed to forms later described, unless such characteristics are obviously inapplicable or unless specific exception is made.

In FIG. 1, two identical implants 10 are illustrated that are positioned at, or slightly inside the cuspid region of the user's lower jaw to be well clear of the nerve canals 12. As shown by the model in FIG. 5, each of the implants 10 carries one part 14 of a snap connector structure. The companion parts 16 are carried by the underside of an overlay denture 18.

FIG. 2 illustrates the implant position relative to the patient's mouth. The implant 10 (FIG. 3) comprises a generally cylindrical biocompatible metal screw anchor 20 and a plastic pillar 22. The anchor 20 is installed in a recess prepared in the cancellous bone tissue 26. The recess comprises two parts. The upper part 28 is formed as a simple cylindrical hole of nominal diameter to a depth of seven or eight millimeters beneath the bone crest 30. The lower part 32 of the recess is a deep annular kerf or channel bounded on the inside by a bone core 34 and on the outside by a cylindrical surface of the same diameter as the upper recess part 28.

The anchor 20 fits the prepared recess. The lower part of the anchor 20 is in the form of an inverted hollow core 36 open at its lower end. The core 36 together with a central partition wall 38, caps the bone core 34. The intermediate portion of the anchor 20, just above the partition 38, is provided with three turns of self-tapping threads 40 that engage the wall of the upper recess part 28. The threads 40 immediately provide a firm connection to the jawbone. The outside diameter of the core 36 equals the inside diameter of the threaded portion.

The upper neck end of the anchor 20 is cylindrical and has a diameter about equal to the inside diameter of the threads 40. The neck projects slightly as, for example, about one millimeter above the bone crest 30 so that the gum tissue 42 can readily cap it. In order to rotate the anchor 20 into position, a wrench (not shown) fits a relatively deep hexagonal socket 44 (see also FIG. 4) at the top of the anchor 20. The socket extends to the partition 38. The major diameter of the socket may be about three and one-quarter millimeters. If the neck of the anchor is trimmed for purposes to be explained more fully hereinafter, the socket 44, deep as it is, remains functional.

The anchor 20 is sized to fit the available jawbone as determined in advance by a method hereinafter described. By this method, the threads will be placed at least one millimeter below the bone crest and preferably more, so that the thread channels are not conduits or receptacles for contaminants. One of two standard anchors is selected—one of larger diameter, say 5.5 millimeters and the other say 4.5 millimeters. Both have an overall length of 16 millimeters with a 5 millimeters neck, 3.5 millimeters of threads, and 7.5 millimeters of core. If a jawbone of quite ample depth is to be fitted, a trephine drill 48 cuts a circular channel to a depth corresponding to the sum of the lengths of the threads and the neck, less one millimeter for projection above the bone. Thus, at A in FIG. 17, the upper recess part 28 is drilled to a depth of 7.5 millimeters, leaving the bone core 50, as at B. The core 50 is carefully broken off by a tool 52, as at C. The bottom of the recess 28 is levelled off by scraping, as at D. The lower recess part 32 is now prepared to a depth of 7.5 millimeters, as at E, leaving the bone core 34 in place, as at F. The anchor 20 can now be installed, as at G.

In the example of FIG. 18, the jawbone is less ample and the maximum recess depth of 13 millimeters is determined. The neck is simply shortened two millimeters to 5.5 millimeters, and the upper recess part correspondingly formed to that depth, as indicated at A, B, C and D in FIG. 18. The lower recess part 32 is formed to the maximum depth as in the previous example. The threads 40 are located an adequate distance between the crest 30.

In the example of FIG. 19, the maximum recess depth is 9.5 millimeters. The core is shortened 2.5 millimeters and the neck is shortened 3 millimeters. Circular gauge markings on the neck of the anchor 20, as well as a circular gauge marker on the core 36, facilitate trimming before surgery. Circular gauge markings on the drill assist in accurately sizing the recess.

The advance study to determine the anchor size begins with a panoramic x-ray which typically magnifies about ten percent (10%). A transparency depicting six modifications of an anchor is provided on a corresponding scale so that by juxtaposition of the two, a suitable anchor configuration can be selected. A drawing of such a transparency is shown in FIG. 20.

The following chart indicates the required modifications of the standard anchor in order to obtain the selected modification:

| MODIFI- CATION # | AVAILABLE BONE | SHORTEN NECK | REMOVE ONE ROW OF VENTS | PREPARE IMPLANT SITE WITH 7½mm CORE DRILL. | |
|---|---|---|---|---|---|
| | | | | STAGE I CORE LINES | STAGE II SHANK LINES |
| 1 | 15mm+ | 0 | 0 | FULL DEPTH TOP LINE | FULL DEPTH TOP LINE |
| 2 | 14mm | −1mm | 0 | 2nd LINE | 2nd LINE |
| 3 | 13mm | −2mm | 0 | 3rd LINE | 3rd LINE |
| 4 | 12mm | −3mm | 0 | BOTTOM LINE | 4th LINE |
| 5 | 11mm | −2mm | −2 & ½mm | 3rd LINE | 5th LINE |
| 6 | 10mm | −3mm | −2 & ½mm | BOTTOM LINE | BOTTOM LINE |

While the self-tapping screw threads 40 provide an immediate mechanical connection to the jawbone, the mechanical connection is completed in a positive manner by growth or regrowth of bone tissue. For this purpose, the anchor core 36 has three rows of perforations 52 about its entire area (See FIGS. 3 and 4). Bone and blood tissues on the inside and outside of the core 36 will link up through the holes 52. The thickness of the core wall being small, bridging of blood vessels and bone tissue will begin in a relatively short time. Mechanical connection is furthermore provided by the intimate adaptation of the walls of the prepared bone cavity and the outer surface of the anchor, both being of equal diameter.

The first or uppermost turn of the threads 40 forms a stop to isolate the lower regions of the anchor 20 from infiltration of foreign matter. By the time, if ever, that resorption occurs at the region of the threads 40, bone tissue will have grown about the anchor neck and through the perforations 52 at the core 36, ensuring a lasting, well anchored implant.

In FIG. 8 there is illustrated an anchor 100 that is similar to the anchor 20 shown in the form of FIG. 4, except that the screw threaded portion 102 of the anchor 100 is moved to the lower core region. Perforations 104 are formed through the screw thread portion. This thread arrangement allows the anchor to be accommodated in a very small receptor site.

The receptor site may be closed to allow a healing period of some number of weeks before a pillar 22 (FIG. 3) of proper size is cemented to the socket 44. The pillar 22 is sized to fit the depth of the socket 44 as by the aid of gauge marks 53.

My preferred attachment comprises a ball 54 (see also FIG. 6) and snap socket 56. The socket 56 is formed at the head or platform 58 of the pillar 22. The pillar 22 provides a neck 60 just above the top of the anchor 20 (FIG. 3) and about which the gum tissue can grow. The head 58 of the pillar 22 projects only about 3 millimeters above the gum tissue so that lateral force exerted by the ball 54 on the socket 56 acts over a very short lever arm. The small torque is effectively resisted by the anchor.

The ball 54 is formed at the lower end of a connector 62. The connector is attached to a downwardly opening recess 64 of the denture 18. The denture recess 64 surrounds the pillar head 58 with ample clearance. The socket 56 has a restricted opening 66 that engages a neck 68 at the base of the ball 54. The depth of the socket 56 provides one-half a millimeter of clearance relative to the ball when the denture is in place. This ensures that the bit force is transmitted via the denture to the gum tissue 42, bypassing the implant in the transmission of such force. Yet, the socket 56, together with the socket of the companion implant, provide the requisite lateral stability and retention.

The connector 62 in the present instance has a series of annular ribs 70 for locking to the denture structure. The connector 62 may be made of plastic such as CELCON brand acetal copolymer of the Celanese Corporation.

The impression of the lower jaw is made with the preferred socketed pillar (FIG. 6) placed in the socket 44 of the anchor 20. A spacer 72 is placed on top of the pillar so that as the impression is made, the ball 54 is at its nominal position at the top of the socket. By the aid of the impression, and in a well understood manner, the lower denture is made with the connector 62 accurately located.

The material of which the pillar 22 is made has suitable density, resilience and flexibility. CELCON has a flexural modulus that closely approaches that of normal bone tissue. The flexibility of the pillar may be made more or less, depending upon the nature of the particular case. For example, if the depth of the implant is necessarily restricted, or if the bone tissue is weak, then flexibility can be added to the pillar in order to minimize the load by increasing the height of the head or reducing the neck 60.

The acetal copolymer ball 54 and the pillar 22 interact in a manner to dissipate the forces under occlusal function. The flexibility is achieved apart from the metal anchor 20, which is itself rigid and which is rigidly affixed to the jawbone.

The pillar can be prepared for other attachments. Thus, the unprepared pillar 74 shown in FIG. 7 provides a head 76 ready for adaptation. FIGS. 9 and 10, respectively, illustrate pillars prepared to serve as attachments sold under the trademarks or trade names SCODENCO and ZEST. In FIG. 9, a male connector part is secured to the pillar. In FIG. 10, a female connector part is secured to the pillar. UDEL® brand polysulfone sold by Union Carbide Corporation is quite suitable for the connectors of FIGS. 9 and 10, since this material provides good bonding and cutting characteristics. FIG. 11 illustrates a model with a bar 80 secured to two of my implants. The bar 80 cooperates with two clips 82 of the denture. One bar attachment of this configuration is known as the PRECIHORIX.

A slightly modified pillar can be used in the same manner as a prepared tooth for supporting a crown or a bridge. Thus, FIG. 12 illustrates a bridge 90 anchored at one end by a prepared natural first bicuspid 92, and at the other end, by a pillar 94. The pillar 94, in this instance, has a frusto-conical head 96 (see also FIG. 13) that corresponds to the prepared tooth. The pillar 94 is secured to the previously described screw anchor 20. Gauge marks 98 on the pillar 94 (FIG. 13) facilitate requisite trimming. The pillar 94 obviously can be used to support a crown or other prostheses.

DESCRIPTION OF DRILL

The drill 120 shown in FIGS. 14, 15 and 16, has an inverted cylindrical cup 122 with teeth 123 at its lower end. The shank 124 of the drill 120 connects to a latch-type slow speed contra angle hand piece (not shown). The shank has a through passage 126 to allow movement of a cooling fluid. Both the cup 122 and the shank 124 have circular markings 128 and 130 so that the depth of cut can be gauged. The part of the cup below the markings 128 is provided with peripheral ridges 132 that slant upwardly to guide material outwardly. Fluid that enters the drill cup via passage 126 may move out through holes 127 in the cup 122. Some fluid may move downwardly to the teeth 123, and then outwardly and upwardly along the flow channels formed by the ridges 132.

The interior diameter of the cup recess 134 increases from a minimum at the teeth 123 so that good running clearance is provided as the bone core is formed. The exterior surface of the cup 122 is reduced at the upper region to provide good running clearance with the jawbone recess being formed.

Intending to claim all novel, useful and unobvious features shown or described, I make the following claims:

1. A two part endosseous implant designed to be secured at a recess prepared in the cancellous bone tissue of a subject, said recess having an outer part substantially in the form of a cylindrical hole, and having an inner part substantially in the form of a cylindrical kerf forming a bone core:
   (a) one of said implant parts comprising an anchor having an inverted core open at its lower end, and peripherally perforated, said inverted core being adapted to encompass a said bone core;
   (b) said anchor having a plurality of turns of self-tapping screw threads adapted to engage the wall of said bone recess;
   (c) said anchor having a cylindrical neck portion above said screw threads having a diameter approximating the inside diameter of said screw threads and of a length sufficient to project just above the bone crest;
   (d) said anchor neck having a non-circular socket cooperable with a tool by the aid of which said anchor is threaded into said bone recess;
   (e) the other of said parts comprising a pillar fitted into said anchor recess;
   (f) said pillar projecting just above the top of said anchor to form or to support a dental restoration or the like.

2. The endosseous implant as set forth in claim 1 in which said anchor has gauge marks by the aid of which said anchor is fitted to the bone recess of the subject.

3. The endosseous implant as set forth in claim 1 in which said pillar is made of semi-rigid plastic material having both resilience and limited flexibility, said pillar having a neck at the region just above the top of said anchor to provide controlled lateral flexibility.

4. The endosseous implant as set forth in claim 3 in which said pillar provides a platform with a snap-in ball socket having a restricted opening to form said one of two companion connector structures; and a denture fitted to the subject's gum and having a ball entering said socket to stabilize said denture, said socket providing an extended stress-free space beneath the ball when the denture is in its nominal position.

5. The endosseous implant as set forth in claim 1 in which said pillar provides a frusto-conical head simulating or approximating a prepared tooth stump.

6. The endosseous implant as set forth in claim 5 in which said pillar is made of a suitable plastic material and of an appropriate neck diameter and head design to simulate the mobility commonly found in slightly mobile natural teeth.

7. The endosseous implant as set forth in any of claims 1 to 6 in which said threads are formed just above said inverted core.

8. The endosseous implant as set forth in any of claims 1 to 6 in which said threads are located at said inverted core, said perforations extending between said threads.

9. An endosseous implant anchor designed to be secured at a recess prepared in the cancellous bone tissue of a subject, said recess having an outer part substantially in the form of a cylindrical hole, and having an inner part substantially in the form of a cylindrical kerf forming a bone core:
   (a) said anchor having an inverted core open at its lower end and peripherally perforated, said anchor core being adapted to encompass said bone core;
   (b) said anchor having a plurality of turns of self-tapping screw threads adapted to engage the wall of said bone recess;
   (c) said anchor having a cylindrical neck portion above said screw threads having a diameter approximating the inside diameter of said screw threads and of a length sufficient to project just above the bone crest;
   (d) said anchor neck having a non-circular socket cooperable with a tool by the aid of which said anchor is threaded into said bone recess.

10. The endosseous implant as set forth in claim 9 in which said anchor has gauge marks by the aid of which said anchor is fitted to the bone recess of the subject.

11. The endosseous implant as set forth in either of claims 9 or 10 in which said threads are formed just above said inverted core.

12. The endosseous implant as set forth in either of claims 9 or 10 in which said threads are located at said inverted core, said perforations extending between said threads.

13. The method of fitting to the mouth of a subject, a dental implant anchor having an inverted hollow core, a plurality of turns of threads and a neck above the threads having a diameter at least approaching the root diameter of the threads, and a non-circular socket extending downwardly from the top of the anchor:
   (a) surveying by radiographic study the size of available jawbone structure;
   (b) determining the maximum recess depth for said anchor;
   (c) sizing both the top and bottom of the anchor as necessary in order to determine an anchor size in which the top of the anchor projects approximately a millimeter above the jawbone with the anchor threads at a position to be located beneath the crest of the jawbone;

(d) forming a jawbone recess in at least two stages, the first stage comprising the formation of an upper cylindrical part of the jawbone recess to a depth determined by said survey, and the second stage comprising the formation of a cylindrical bone core beneath said upper recess part by an annular cut to a depth determined by said survey;

(e) thereafter placing the sized anchor in the jawbone recess by rotating the anchor by means of a tool inserted in said non-circular socket.

14. The method as set forth in claim 13 together with the step of fixing in said socket a pillar having a head located just above the top of said anchor for cooperation with dental prosthesis.

15. An endosseous implant anchor designed to be secured at a recess prepared in the cancellous bone tissue of a subject, said recess having an outer part substantially in the form of a cylindrical hole, and having an inner part substantially in the form of a cylindrical kerf forming a bone core:

(a) said anchor having an inverted core open at its lower end peripherally perforated, said anchor core being adapted to encompass said bone core;

(b) said anchor having a plurality of turns of screw threads adapted to engage the wall of said bone recess;

(c) said anchor having a substantially cylindrical neck portion above said screw threads having a diameter not greater than the inside diameter of said screw threads and of a length sufficient to project just above the bone crest;

(d) said anchor neck having means cooperable with a tool by the aid of which said anchor is threaded into said bone recess;

(e) said anchor neck having an upwardly opening recess for placement of a companion part.

16. The endosseous implant as set forth in claim 15 together with a pillar fitted to said anchor recess to form or to support a dental restoration or the like.

17. The endosseous implant as set forth in claims 15 or 16 in which said anchor recess is non-circular to comprise said tool cooperable means.

18. The endosseous implant as set forth in claims 15, 16, or 17 in which said anchor has gauge marks by the aid of which said anchor is fitted to the bone recess of the subject.

19. The endosseous implant as set forth in claims 15, 16, or 18 in which said threads are formed just above said inverted core.

20. The endosseous implant as set forth in any of claims 15 to 18 in which said threads are located at said inverted core, said perforations extending between said threads.

21. The endosseous implant as set forth in claims 19,20,21,22,23 or 24 in which said pillar is made of semi-rigid plastic material having both resilience and limited flexibility, said pillar having a neck at the region just above the top of said anchor to provide controlled lateral flexibility.

22. The endosseous implant as set forth in claim 21 in which said pillar provides a platform with a snap-in ball socket having a restricted opening to form said one of two companion connector structures; and a denture fitted to the subject's gum and having a ball entering said socket to stabilize said denture, said socket providing an extended stress-free space beneath the ball when the denture is in its nominal position.

23. The endosseous implant as set forth in any of claims 16 to 20 in which said pillar provides a frusto-conical head simulating or approximating a tooth prepared for a dental prosthesis.

24. The endosseous implant as set forth in claim 23 in which said pillar is made of plastic material to simulate the mobility of natural teeth.

* * * * *